United States Patent [19]
Berry et al.

[11] Patent Number: 4,686,694
[45] Date of Patent: Aug. 11, 1987

[54] PROBE FOR AN APPARATUS FOR ANALYZING METALS BY X-RAY FLUORESCENCE

[75] Inventors: Peter F. Berry; Wendell D. Miller; John L. Nethery, Jr., all of Austin, Tex.

[73] Assignee: Ramsey Engineering Company, St. Paul, Minn.

[21] Appl. No.: 216,228

[22] Filed: Dec. 15, 1980

[51] Int. Cl.$^4$ .................. G21K 5/02; G01N 23/223
[52] U.S. Cl. .................... 378/120; 378/45; 250/498.1
[58] Field of Search .............. 378/4, 7, 44, 45, 120, 378/140, 150, 161; 250/498.1

[56] References Cited
U.S. PATENT DOCUMENTS

| 3,141,976 | 7/1964 | MacIntyre | 250/498.1 |
| 3,177,364 | 4/1965 | Green | 250/498.1 |
| 3,889,113 | 6/1975 | Rhodes | 378/45 |
| 4,167,674 | 9/1979 | Koontz et al. | 378/161 |
| 4,178,513 | 12/1979 | Dubois et al. | 378/45 |

Primary Examiner—Bruce I. Anderson
Assistant Examiner—Jack I. Berman
Attorney, Agent, or Firm—Norvell & Associates

[57] ABSTRACT

An apparatus for analyzing metal alloys includes an electronic unit connected to a hand-held probe unit. The probe unit includes a radiation detector enclosed in a detector housing and a radiation source enclosed in a source housing. The detector housing is generally cylindrical in shape and has an aperture formed in its sidewall. The source housing is formed as a hollow, generally right triangular prism with an open base attached to the detector housing over the aperture and tapering to a tip having an aperture formed therein. The triangular shape of the source housing permits contact measurements in hard to get at places. A shutter drive mechanism is utilized to move a shutter means between a first position blocking radiation and a second position passing radiation from the source to the aperture in the tip of the source housing. Radiation from the source generates X-rays from a sample of material to be analyzed which X-rays pass through the aperture in the tip of the source housing and the aperture in the side wall of the detector housing to the radiation detector.

15 Claims, 8 Drawing Figures

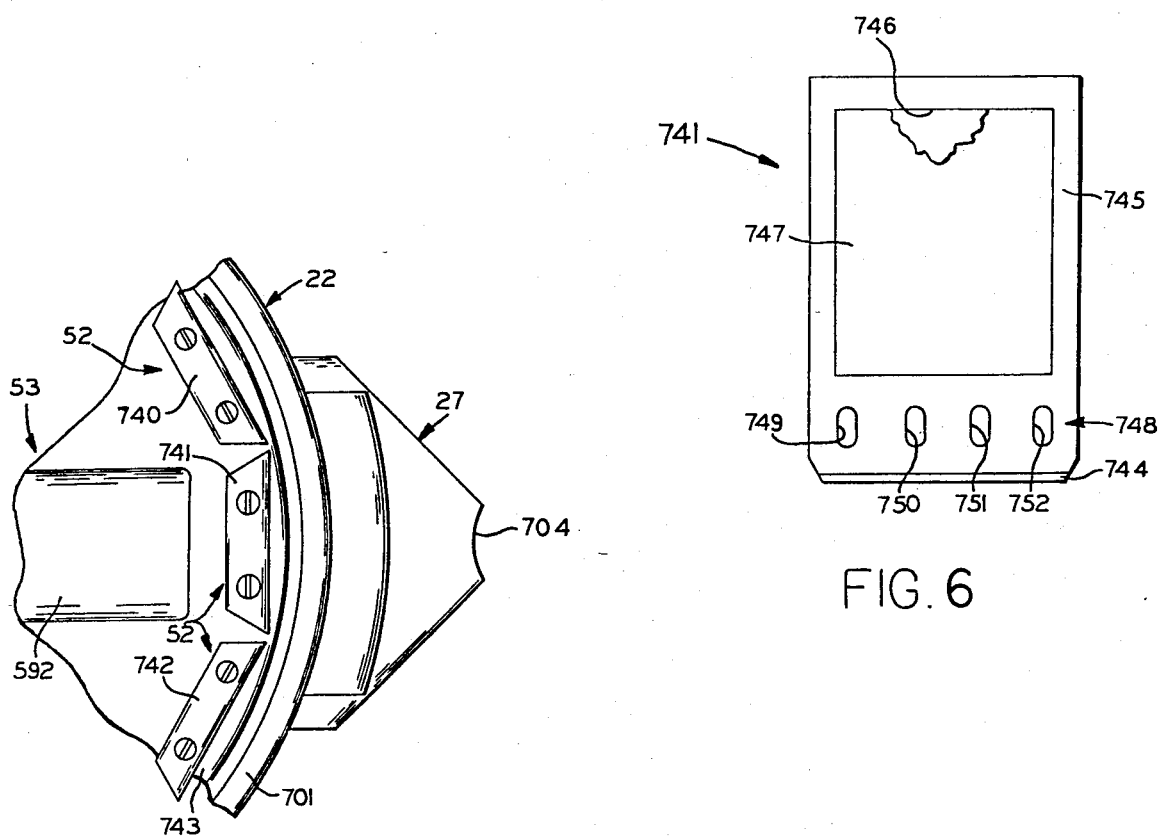
FIG. 5
FIG. 6
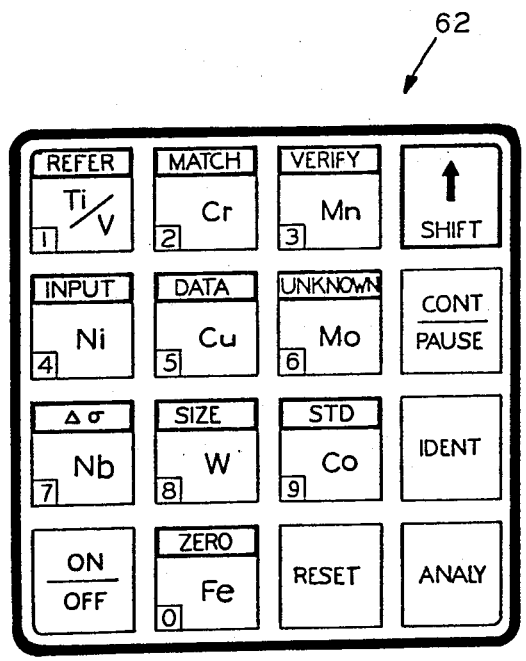
FIG. 7

PROBE FOR AN APPARATUS FOR ANALYZING METALS BY X-RAY FLUORESCENCE

CROSS-REFERENCE TO RELATED APPLICATIONS

This application is related in subject matter to the following co-pending applications: Ser. No. 216,226, filed Dec. 15, 1980, now abandoned, entitled: "Filter Means For An Apparatus For Analyzing Metals By X-Ray Fluorescence" (TN-13-PA-US) and U.S. Pat. No. 4,429,409, entitled "Portable Apparatus For Analyzing Metals By X-Ray Fluorescence" (TN-15-PA-US) and assigned to the same assignee as this application.

BACKGROUND OF THE INVENTION

1. Field of the Invention

The present invention relates to a device for the identification of metal alloys by the X-ray fluorescence method.

2. Description of the Prior Art

Many businesses manufacture products from stock pieces of metal alloys purchased from a manufacturer of such stock. If several different alloys having a similar appearance are being stored and utilized in the daily manufacturing process, a mixed material problem can occur. If the wrong alloy is utilized in the manufacture of a part, it may result in the premature failure of the part during normal use. Such a failure has the potential for serious economic consequences and physical danger.

As businesses became aware of the mixed metals problem, they turned to quantitative inspection techniques including X-ray fluorescence. Many types of devices for X-ray flourescence analysis are known. Radiation is emitted by a sealed radioactive source and impinges upon the sample being tested. The radiation initiates the emission of secondary X-radition from the sample. The secondary X-radiation is sensed and the concentration of any element in the sample is determined by the intensity of the characteristic X-rays of the element in the spectrum. Use can be made of special filters which make it possible to eliminate certain spectral lines so that only those that are typical of a given element are permitted to remain. Thus, by using a series of different filters, it is possible to determine the composition and concentration of the constituents of any sample.

U.S. Pat. No. 3,992,542 discloses an apparatus for the continuous analysis of samples. The apparatus includes a measuring head having a radioactive source and a counting assembly connected to the radiation detector. A sequential filter transfer unit has a conveyor driven in reciprocating motion between a filter stack and a gap between the source and the detector. A sample transfer unit with inclined parallel slide ramps and a receiving trough fitted with a push plate for passing the sample in front of the source in unitary sequence is controlled by a mechanical control assembly and an electronic assembly for recording signals delivered by the radiation detector after analysis of each sample. However, such a device has the disadvantage of requiring a sample to be brought to the device for analysis. Furthermore, the sample must be in a certain size range in order to be passed in front of the radioactive source.

SUMMARY OF THE INVENTION

The present invention concerns an apparatus for analyzing a sample of material by the X-ray fluorescence method. The apparatus includes a source of X-ray radiation, a radiation detector, and a plurality of filters adapted to preferentially pass the spectral lines of a predetermined one of a plurality of different elements, positioned in a hand-held probe connected to an electronic unit. The probe includes a hollow, generally cylindrical detector housing enclosing the radiation detector and the filters and a hollow, generally right triangular prism shaped source housing enclosing the radiation source.

The source housing tapers from an open base attached to the detector housing to a tip having an aperture formed therein. A pair of radioactive sources are positioned in the housing adjacent and on either side of the tip aperture. Each source is enclosed by a collimator having an exit port directed toward the tip aperture and each collimator is enclosed by a shutter means moveable between a first position blocking radiation and a second position passing radiation from the source to the tip aperture. Radiation from the sources generates X-rays from the sample which X-rays pass through the aperture in the tip and the open base of the source housing and enter the detector housing through an aperture formed therein.

BRIEF DESCRIPTION OF THE DRAWINGS

FIG. 5 is a fragmentary top plan view of the probe housing of FIG. 1 showing the radiation detector and filter brackets.

FIG. 6 is a side elevational view of one of the filter brackets of FIG. 5.

FIG. 7 is a plan view of the electronic unit keyboard of FIG. 2.

DESCRIPTION OF THE PREFERRED EMBODIMENTS

The present invention relates to an apparatus for rapid, non-destructive on-site verification of type and elemental composition of important engineering alloys. The apparatus uses radioisotope excited X-ray fluorescence to analyze a sample in any one of a variety of physical forms, such as pipes, plates, welds, and welding materials, machined parts, castings, etc. The sample to be analyzed is exposed for a few seconds to radiation from a radioisotope source. The atoms of some elements in the material are caused to fluoresce and emit X-rays which are characteristic of the element. The detector system separates X-rays coming from the sample into discrete energy regions and, from a measure of the intensity in each region, determines the element concentrations. The energy regions corresponding to the elements: Ti, V, Cr, Mn, Fe, Co, Ni, Cu, Nb, Mo and W, are effectively analyzed.

Figure 1:
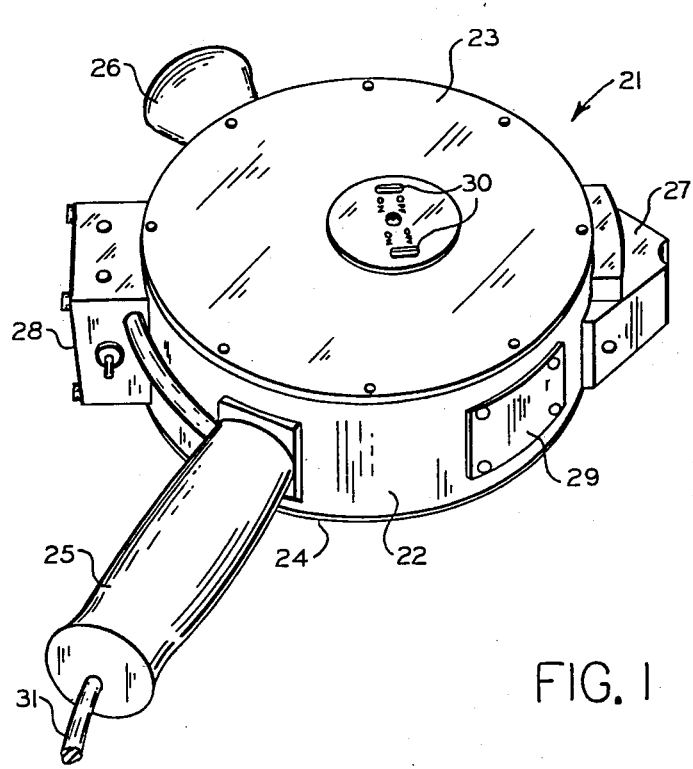
FIG. 1 is a perspective view of the probe of a metal analyzing apparatus according to the present invention.

There is shown in FIG. 1 a metal analyzing probe apparatus 21 according to the present invention. A radioisotope source, a detector, and control circuitry are contained in a generally cylindrical housing 22. The housing has open upper and lower ends which are closed by a top cover 23 and a bottom cover 24 respectively which are attached to the sidewall of the housing by suitable fasteners. A handle 25 and a knob 26 are attached to the sidewall of the housing at spaced-apart positions to define an included angle of less than 180°. A source housing 27 and an end housing 28 are attached to the sidewall of the housing 22 and spaced approximately 180° apart. The source housing 27 and the end housing 28 are each approximately equally spaced between the handle 25 and the knob 26. As will be discussed below, a plate 29 is attached to the sidewall of the housing 22 to cover a filter access port and a pair of source shutter position tags 30 are positioned in the top cover 23. There is attached to the handle 25, electrical lines 31 which are connected to an electronic unit (not shown) including a power source for communication with and supplying power to the circuitry enclosed in the housing 22.

Figure 2:
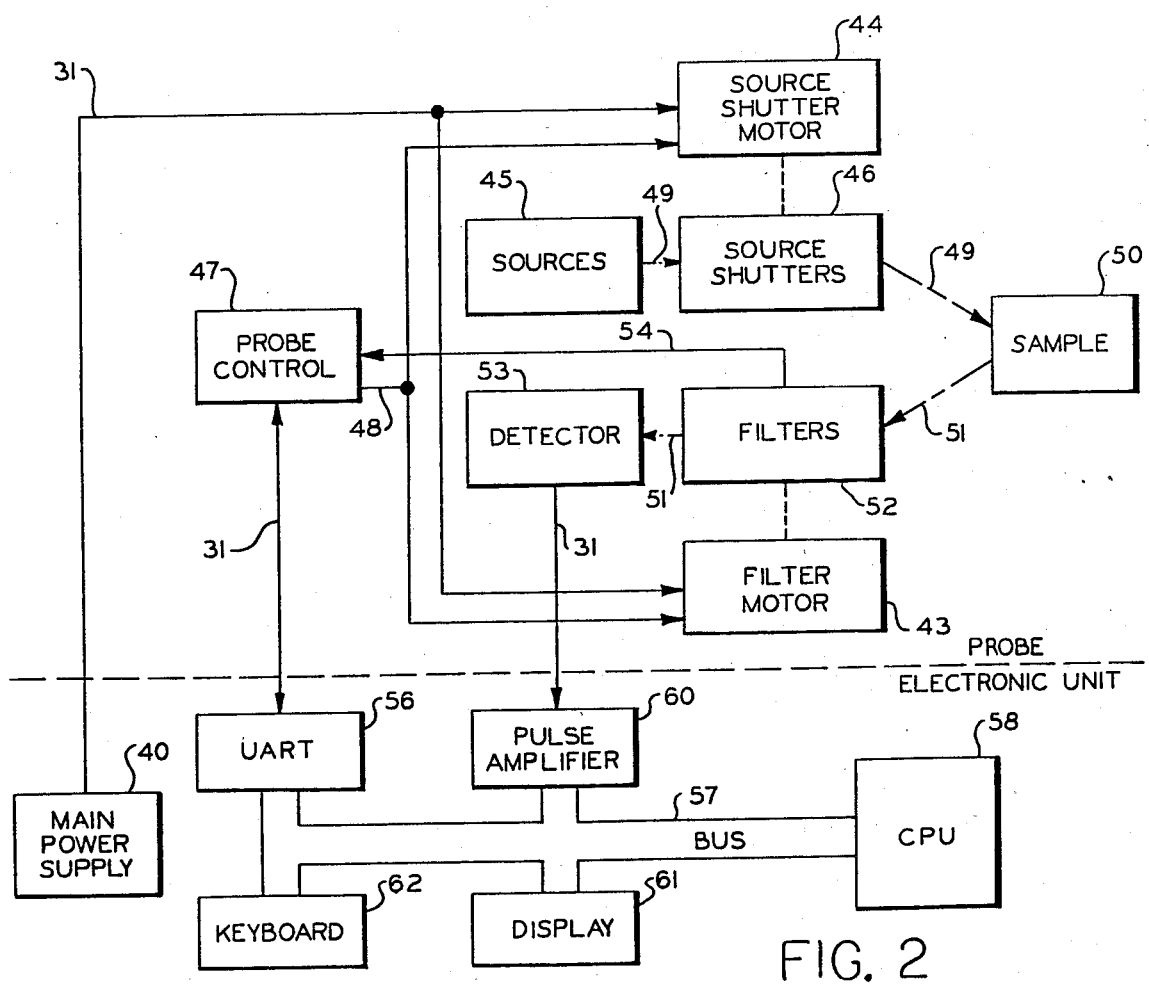
FIG. 2 is a block diagram of the metal analyzing apparatus according to the present invention.

A block diagram of the circuitry contained in the probe housing 22 of FIG. 1 and the associated electronic unit is illustrated in FIG. 2. A main power supply 40 in the electronic unit generates various voltages on the power lines 31. The line 31 is connected to a filter motor 43 and a source shutter motor 44.

The source housing 27 of FIG. 1 contains a pair of radioisotope sources 45. The sources 45 are positioned behind source shutters 46 which are mechanically controlled by the source shutter motor 44. A probe control circuit 47 generates control signals on a line 48 to actuate the source shutter motor 44 to open and close the source shutters 46. When the source shutters 46 are opened, radiation 49 from the sources 45 impinges upon a sample 50. X-rays 51 are emitted from the sample 50 and passed through one of a plurality of filters 52 to a detector 53. A signal representing the one of the filters 52 positioned between the sample 50 and the detector 53 is generated on a line 54 through the probe control circuit 47.

The probe control circuit 47 generates signals representing the operating conditions of the circuit on one of the lines 31 to a communications UART 56. The UART 56 is connected to a bus 57. Also connected to the bus 57 is a central processing unit CPU 58. The detector 53 generates an output signal on one of the lines 31 which is connected to a pulse amplifier 60. The pulse amplifier 60 generates an output signal to the bus 57. The output signal represents the X-ray intensity transmitted through one of the filters 52 to the detector 53. The CPU 58 reads the X-ray information and the filter identification from the bus lines 57. After the CPU 58 has read this information for one or more of the filters 52, it then determines the composition of the sample 50.

The CPU 58 includes a memory in which are stored the X-ray data from a plurality of alloys. The CPU compares the data for the sample 50 with the stored data until a match is found. If no match is found, the CPU 58 so indicates. The CPU 58 then generates output signals onto the bus 57 to a display 61 for a visual display of the identification of the alloy and its elemental contents. A keyboard 62 is connected to the bus 57 for communicating with the CPU 58 to generate control signals through the UART 56 to the probe control circuit 47. The probe control circuit 47 responds by controlling the filter motor 43 and the source shutter motor 44.

Figure 3:
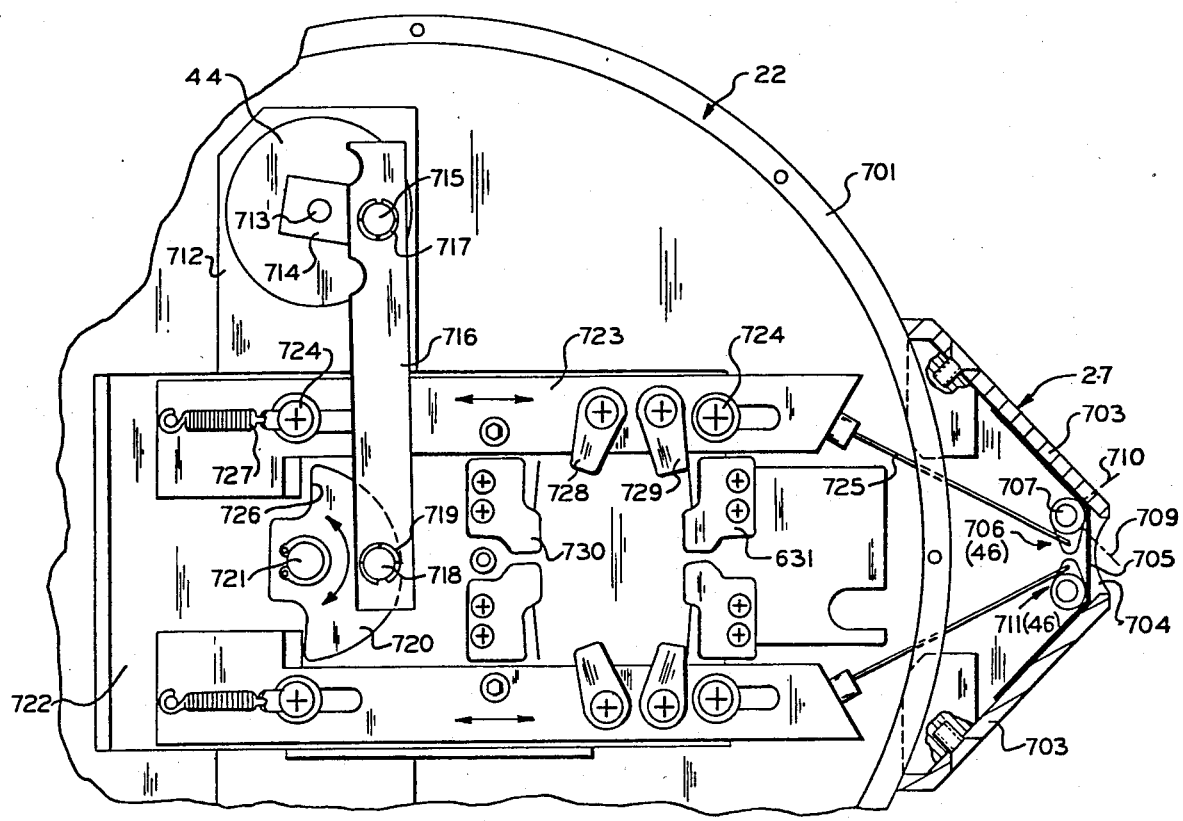
FIG. 3 is a fragmentary top plan view of the probe housing of FIG. 1 showing the source shutters and shutter drive mechanism.
Figure 4:
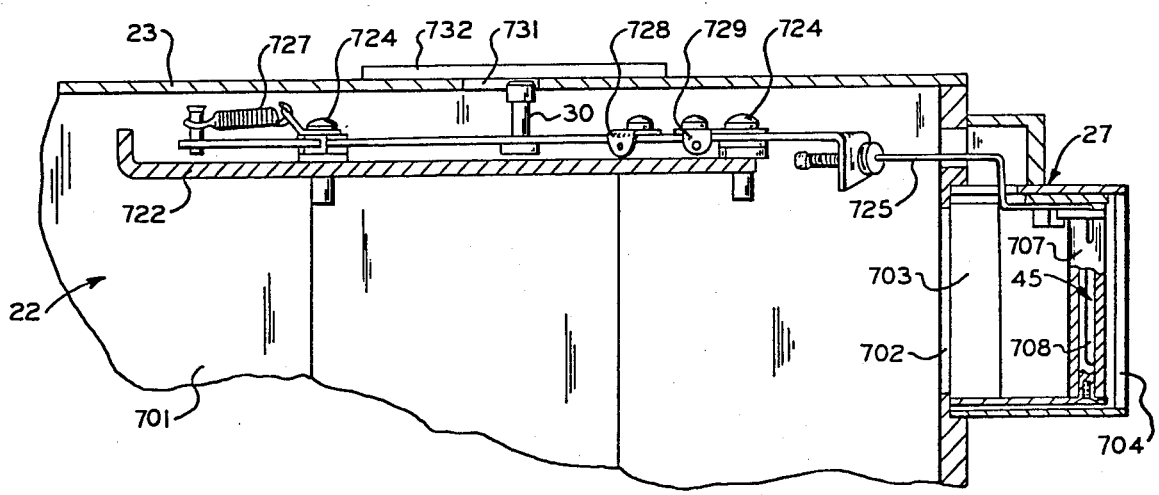
FIG. 4 is a fragmentary side elevational view of the probe housing of FIG. 1 showing the source shutters and shutter drive mechanism.

There is shown in FIG. 3 a top plan view of the probe housing of FIG. 1 with the top cover 23 and the top of the source housing 27 removed. In the interest of clarity, only the source shutters and the shutter drive mechanism are shown. There is shown in FIG. 4 a fragmentary side elevational view of the probe housing of FIG. 1 with only the source shutters and the shutter drive mechanism shown in the interest of clarity. The detector housing 22 includes a cylindrical side wall 701 in which is formed an aperature 702 for passing X-rays from the sample material to the radiation detector (not shown). The source housing 27 is attached to the outside of the side wall 701 by suitable means. The source housing 27 has a body formed as a right triangular prism, triangular in cross-section, with a pair of side walls 703 tapering from an open base at the aperture 702 to a tip forming a narrow aperture 704. The aperture 702 is covered by a "window" which typically is formed of facing sheets of Mylar material and polypropylene material which are attached to the inside surfaces of the side walls 703. The window material is pervious to the radiation from the source and the sample.

A first shutter means 706 (one of the shutters 46 of FIG. 2) has a generally tubular body 707 which is rotatably mounted at its ends to the top and bottom of the source housing 27. A generally tubular collimator and source holder 708 is mounted inside the shutter 707 and is stationary with respect to the source housing. Radiation from the source 45 can only exit the collimator through a port along a line 709. The radiation can only exit the shutter through a shutter port along a line 710 which is generally positioned at right angles with respect to the line 709 when the shutter is in the closed position as shown in FIG. 3. As will be discussed, when the shutter is rotated in a clockwise direction by the shutter drive motor 44, the shutter port is in axial alignment with the collimator port and radiation from the source exits through the window 705 along the line 709.

A second shutter means 711 (one of the shutters 46 of FIG. 2) is positioned adjacent the other side of the aperture 704 and includes a different radiation source. For example, the shutter means 706 can include an Fe 55 radiation source while the shutter means 711 can include a Cd 109 radiation source.

The shutter drive motor 44 is mounted on a motor support bracket 712 and has an output shaft 713 which is connected to one end of an output arm 714. The other end of the output arm 714 has a pin 715 connected thereto which extends through an aperture in one end of a link arm 716. The link arm 716 is retained on the pin 715 by a snap ring 717. The other end of the link arm 716 is attached to a pin 718, extending through an aperture in the arm, by a snap ring 719. The pin 718 is connected at the periphery of a semi-circular cam 720 which is rotatably mounted on a shaft 721 attached to a shutter plate 722. A shutter slide 723 is mounted for longitudinal movement on the shutter plate 722 by a pair of guides 724 attached to the shutter plate 722 and extending through elongated apertures formed in the shutter slide 723.

The end of the shutter slide 723 adjacent the source housing 27 has one end of a wire link 725 attached thereto, the other end of the wire link being attached to an arm extending from the side of the shutter 707. When the drive motor 44 is rotated in the counterclockwise direction as viewed in FIG. 3, the cam 720 is also rotated in the counterclockwise direction. An end 726 of the cam 720 engages the camming surface on the shutter slide 723 and forces the shutter slide in a direction away from the source housing 27. The movement of the shutter slide 723 is transmitted through the wire link 725 to rotate the shutter 707 to line up the shutter port with the collimator port. When the motor 44 is rotated back to the position shown in FIG. 3, a return spring 727, connected between the guide 724 adjacent the cam 720 and the shutter slide 723, returns the shutter slide 723 and the shutter 707 to the positions shown.

Attached to the shutter slide 723 are a pair of switch actuating cams 728 and 729. A pair of limit switches, a switch 631 and a switch 730, are attached to the shutter plate 722. The switch 631 is shown in its unactuated state. When the shutter 707 is closed, as is shown in FIG. 3, the switch 631 is actuated by the switch cam 729. The switch 730 is connected in a manner similar to the switch 631. The combination of these two switches 631 and 730 generates signals which indicate that the shutter 707 is in the closed position. When the shutter drive motor 44 actuates the shutter slide 723, the switch cam 728 is moved into contact with the actuating arm of the switch 730 and the cam 729 is moved out of contact with the actuating arm of the switch 631. Thus, the switches 631 and 730 will reverse their signals to indicate that the shutter 707 is in the open position. The second shutter means 711 is actuated in a similar manner and includes similar limit switches for indicating the position of the shutter associated therewith.

The shutter slide 723 has a generally upstanding source shutter position tag 30 attached thereto. The upper end of the tag 30 extends into an elongated aperture 731 formed in the top cover 23 of the probe housing. The movement of the shutter slide 723 moves the tag 30 in the aperture 731 between marked "off" and "on" positions which are shown in FIG. 1. A transparent cover 732 can be attached to the upper surface of the top cover 23 to cover the aperture 731. Although not shown, a similar aperture is provided for the other shutter position tag which is attached to the shutter slide for the other radiation source.

There is shown in FIG. 5, a fragmentary top plan view of the probe housing of FIG. 1 showing the placement of the radiation detector 53 and the filters 52. The radiation detector 53 includes a photomultiplier tube 592 which is positioned to receive X-rays which pass through the aperture 704 and window in the tip of the source housing 27 and through the aperture in the side wall 701 of the detector housing. A plurality of filters 52 include the filter brackets 740, 741, and 742. The brackets are attached to a disc 743 which is rotated beneath the radiation detector 592.

The bracket 741 is shown in a side elevational view in FIG. 6. The bracket 741 is generally L-shaped with a relatively short lower leg 744 attached to the upper surface of the disc 743 by suitable fastners. A generally upstanding leg 745 has a generally rectangular aperture 746 formed therein for receiving a sheet of filter material 747. Each of the filter brackets retains a sheet of different filter material for preferentially passing only the spectral lines of a selected element typically found in the materials analyzed. The bracket 741 also has an indentification means area 748 located between the lower leg 744 and the lower edge of the aperture 746.

The area 748 can have from zero to four apertures 749 through 752 formed therein. The presence or absence of one of the apertures generates a binary coded signal in cooperation with one of the photodiodes and its associated photo transistor. There are sixteen different combinations of blocked and open apertures which can be utilized to identify the particular sheet of filter material which is located between the radiation detector 592 and the sample of material which is positioned at the tip of the source housing 27.

There is shown in FIG. 7 a plan view of the electronic unit keyboard of FIG. 2. The apparatus combines a well established analytical technique, radioisotope X-ray flourescence with microelectronics to accomplish several measurement obJectives. The primary objectives are: verification of alloy grade or type and, composition analysis of a large number of engineering alloys. All measurements can be made with a sample in a variety of physical forms such as pipe, plate, weld and welding material, machine parts, castings, etc. The X-ray flourescence method is a nondestructive method which allows for measurement of many elements with high precision. Alloy identification is accomplished by recognizing the unique combination of several elements in narrowly specified composition ranges. Accurate quantitative analysis is achieved by making appropriate corrections for inter-element matrix effects.

The material to be analyzed is exposed for a few seconds to radiation from one of the radiosotope sources. The atoms of some of the elements of the material are caused to flouresce and emit X-rays which are characteristic of the element. The detector system separates X-rays coming from the sample into descrete energy regions and, from a measure of the intensitry in each region, determines the element concentration. The energy regions correspond to the elements: Ti, V, Cr, Mn, Fe, Co, Ni, Cu, Nb, Mo and W are effectively analyzed. The central processor unit 58 coordinates the operation of the probe with the electronics unit according to instructions contained in the permanent memory. All essential calibration data is stored in this memory. In addition, a second memory is used for data processing and storage of standardization and other factors pertaining to special modes of operation.

The basic modes of operation are alloy identification and analysis. Each mode can be modified for a selected precision sample size comparision, and for other measurement conditions, through the touch-type keyboard 62 on the instrument panel of the electronic unit. Alloy identification is initiated by depressing the IDENT key. The probe is placed in position and the remote switch 656 is actuated. After approximately twenty seconds, if the measured data matched that of one of the library alloys, the alloy type is registered on the display 61. The number of alloys stored in the memory can exceed more than one hundred and includes most engineering alloys of importance. The apparatus enables the determination of the percent content of the elements shown on the keyboard. The content of the elements Ti, V, Cr, Ni, Cu, Nb, Mo and W can be displayed immediately after the identification measurement. These and other elements can also be analyzed specifically to a higher precision with matrix compensation based on the identification data. Alternatively, the alloy type to be analyzed can be entered through the keyboard so that even single element determination can be made with matrix compensated accuracy. A typical analysis takes between ten and twenty seconds. The element symbol is displayed along with the percent content.

Each mode of measurement can be modified by one of the four selectable levels of precision, and one of several size compensation routines. For example, the size compensation feature would correct for undersized samples and non-standard probe-to-sample air gap distances as might be presented by some weld configurations of a non-contact measurement on a high temperature surface. The effect on alloy identification of statistical variations in the measured X-ray intensities is automatically factored into the decision making process. The chance of a mistaken identity is estimated to be less than one in one hundred As for elemental analysis, the precision depends on the element content and the alloy types. Some typical precision values for common alloys are shown in the following table. Precision can be improved by a factor of three when utilizing one of the increased precision modes. Accuracy is usually equal to the precision.

| TABLE OF PRECISION VALUES | |
|---|---|
| ALLOY TYPE | TYPICAL PRECISIONS |
| Low Alloy Steel (e.g. 2.25 Cr, 1 Mo) | ±0.02% (Ti, V, Mo, Nb) ±0.1% (Cr) ±0.3% (Mn) |
| Stainless Steel (e.g. SS304/316) | ±0.03% (Ti, V, Mo, Nb) ±0.3% (Cr, Mn) ±0.5% (Fe, Co, Ni, Cu) |
| Nickel Alloys (e.g. Inconel 625, Hasteloy X) | ±0.04% (Ti, V, Mo Nb, W) ±0.2% (Ni) ±0.35% (Cr, Mn, Cu) ±0.55% (Fe, Co) |

Figure 8:
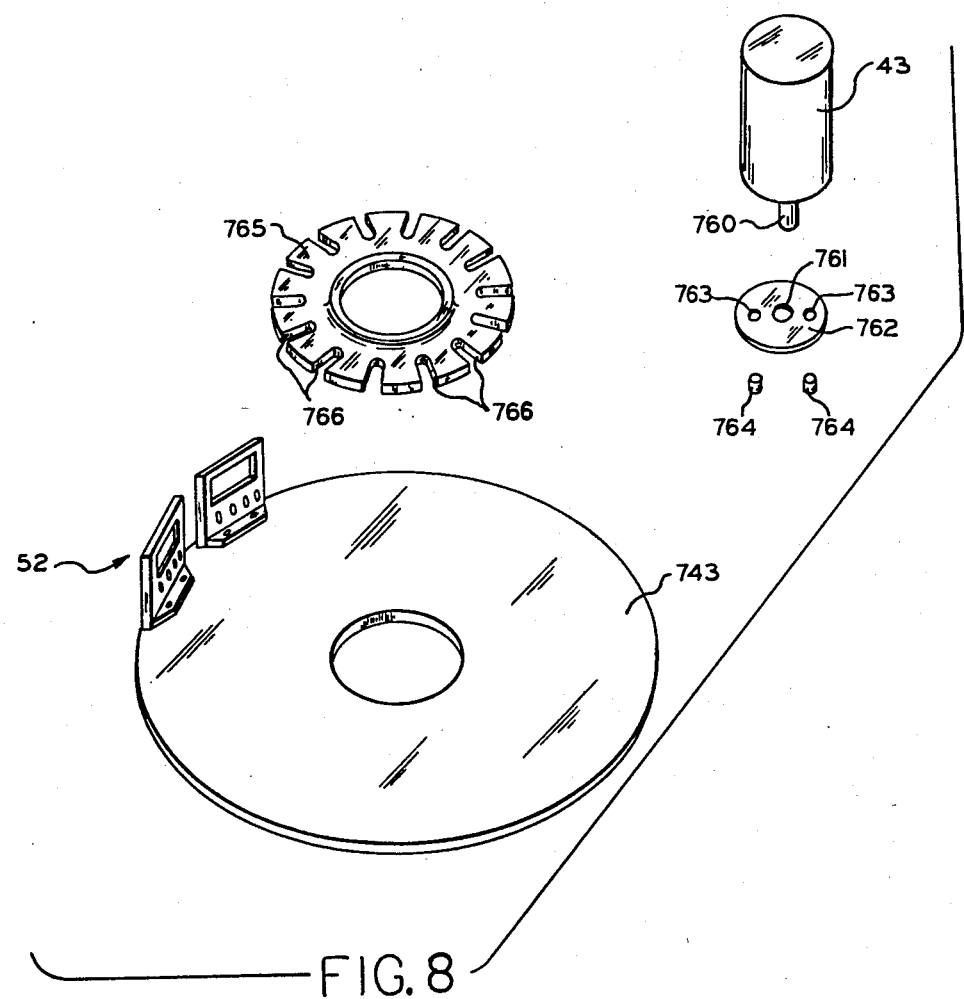
FIG. 8 is an exploded perspective view of the filter drive mechanism including the filters and filter motor of FIG. 2.

There is shown in FIG. 8 an exploded perspective view of the filter drive mechanism of the present invention. The filter drive motor 43 has an output shaft 760 which is retained in a centrally disposed aperture 761 formed in a drive wheel 762. The drive wheel 762 also has a pair of aperture 763 formed therein which are spaced equidistant on either side of the central aperture 761. Each of a pair of drive pins 764 is retained in one of the apertures 763 and extends above the surface of the drive wheel 762 opposite the surface facing the drive motor 43.

A geneva wheel 765 is attached to the filter bracket disc 743 for rotation about a common axis on a bearing (not shown). The periphery of the geneva wheel 765 has a plurality of slots 766 formed therein. The drive motor 43 and drive wheel 762 are positioned such that the drive pins 764 engage alternate ones of the slots 766 as the drive motor 43 rotates the drive wheel 762. Thus, during each one-half revolution of the drive wheel 762 the geneva wheel 765 and the filter bracket disc 743 are rotated a portion of one complete revolution to replace one of the filters 52 with an adjacent one of the filters.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. In an apparatus for analyzing a sample of material by the X-ray fluorescence method having a radiation source for radiating the sample, a radiation detector for receiving X-rays generated from the sample, and a detector housing for enclosing the radiation detector, the detector housing having an aperture formed in a side wall thereof, a source housing comprising: a source housing body formed as a hollow, generally right triangular prism tapering from an open base to a tip having an aperture formed therein; means for attaching said base of said source housing body to the detector housing over the aperture formed in the detector housing; and means for mounting the radiation source adjacent said aperture in said tip of said source housing body whereby, when said tip of said source housing body is positioned adjacent the material sample, radiation from the radiation source passes through said aperture in said tip to radiate the material sample and X-rays generated from the material sample pass through said aperture in said tip and said aperture in the detector housing to the radiation detector in said detector housing.

2. The source housing according to claim 1 including shutter means mounted in the source housing between the radiation source and said aperture in said tip, and means for selectively moving said shutter means between an "off" position blocking radiation and an "on" position passing radiation from the source to the aperture.

3. The source housing according to claim 2 wherein the radiation source includes radioactive means enclosed in a generally tubular collimator having a radiation exit port formed therein facing said aperture in said tip, and wherein said shutter means has a generally tubular body enclosing said collimator and having a port formed therein in axial alignment with said collimator port when said shutter means is in the "on" position.

4. The source housing according to claim 1 including radiation pervious means attached to the interior of said source housing body and covering said aperture in said tip.

5. The source housing according to claim 4 wherein said radiation pervious means is formed of a sheet of Mylar material facing a sheet of polypropylene material.

6. The source housing according to claim 1 wherein the radiation source includes a first radioactive means positioned on one side of said aperture and a second radioactive means positioned on another side of said aperture.

7. In an apparatus for analyzing a sample of material by the X-ray fluorescence method having a radiation source for radiating the sample and a radiation detector for receiving X-rays generated from the material sample, a hand-holdable probe comprising: a detector housing enclosing the radiation detector and having an aperture formed in a side wall thereof adjacent the radiation detector, and a source housing having a body formed as a hollow, generally right triangular prism for enclosing the radiation source, said body tapering from an open base attached to said detector housing over said aperture to a tip having an aperture formed therein, the radiation source being positioned adjacent said aperture in said tip.

8. The probe according to claim 7 including shutter means mounted in said source housing body between the radiation source and said aperture in said tip, and means for selectively moving said shutter means between an "off" position blocking radiation and an "on"

position passing radiation from the radiation source through said aperture in said tip.

9. The probe according to claim 8 including means responsive to said means for moving for indicating when said shutter means is in said "on" and "off" positions.

10. The probe according to claim 9 wherein said means for indicating includes a shutter position indicating aperture formed in a wall of said detector housing and a shutter position tag positioned in said detector housing and visible through said indicating aperture, said tag being coupled to said means for moving for indicating said "on" and "off" positions of said shutter means.

11. The probe according to claim 8 wherein the radiation source includes radioactive means enclosed in a generally tubular collimator having a radiation exit port formed therein facing said aperture in said tip, and wherein said shutter means has a generally tubular body enclosing said collimator and having a port formed therein in axial alignment with said collimator port when said shutter means is in the "on" position.

12. The probe according to claim 7 including radiation pervious means attached to the interior of said source housing body covering said aperture in said tip.

13. The probe according to claim 12 wherein said radiation pervious means is formed of a sheet of Mylar material facing a sheet of polypropylene material.

14. The probe according to claim 7 wherein radiation source includes a first radioactive means positioned on one side and a second radioactive means positioned on another side of said aperture in said tip.

15. The probe according to claim 14 wherein said first radioactive means includes Fe 55 material and said second radioactive means includes Cd 109 material.

* * * * *